US010101961B2

(12) United States Patent
Gao

(10) Patent No.: US 10,101,961 B2
(45) Date of Patent: Oct. 16, 2018

(54) METHOD AND DEVICE FOR ADJUSTING AUDIO AND VIDEO BASED ON A PHYSIOLOGICAL PARAMETER OF A USER

(71) Applicant: Lenovo (Beijing) Co., Ltd., Beijing (CN)

(72) Inventor: Lixin Gao, Beijing (CN)

(73) Assignee: Lenovo (Beijing) Co., Ltd., Beijing (CN)

(*) Notice: Subject to any disclaimer, the term of this patent is extended or adjusted under 35 U.S.C. 154(b) by 3 days.

(21) Appl. No.: 14/976,724

(22) Filed: Dec. 21, 2015

(65) Prior Publication Data
US 2017/0090861 A1 Mar. 30, 2017

(30) Foreign Application Priority Data

Sep. 24, 2015 (CN) .......................... 2015 1 0618003

(51) Int. Cl.
G06F 3/16 (2006.01)
H04S 7/00 (2006.01)
G02B 27/00 (2006.01)
G02B 27/01 (2006.01)
G06F 3/01 (2006.01)
(Continued)

(52) U.S. Cl.
CPC .............. G06F 3/165 (2013.01); A61B 3/113 (2013.01); A61B 5/11 (2013.01); G02B 27/0093 (2013.01); G02B 27/017 (2013.01); G06F 3/013 (2013.01); G06F 3/0482 (2013.01); G06T 19/006 (2013.01); H04S 7/304 (2013.01); G02B 2027/0187 (2013.01)

(58) Field of Classification Search
CPC . G06F 3/01; G06F 3/011; G06F 3/012; G06F 3/013; G06F 3/0482; G06F 3/165; G06F 1/163; A61B 3/113; A61B 5/11; G06T 19/006; H04S 7/303; H04S 7/304; H04S 2420/01; H04N 13/0429; G02B 27/017; G02B 27/0172; G02B 2027/0187
See application file for complete search history.

(56) References Cited

U.S. PATENT DOCUMENTS 5,796,843 A * 8/1998 Inanaga .................. H04S 3/004
381/17
5,959,597 A * 9/1999 Yamada ............... G02B 27/017
345/7

(Continued)

Primary Examiner — Keith Crawley
(74) Attorney, Agent, or Firm — Harness, Dickey & Pierce, P.L.C.

(57) ABSTRACT

An information processing method and an electronic device are provided. The method includes: detecting a first physiological parameter of a user; obtaining a change in the first physiological parameter of the user based on the first physiological parameter of the user; controlling, based on the change in the first physiological parameter of the user, an image outputting unit to output the adjusted image information; determining an audio adjustment parameter for an audio outputting unit based on the change in the first physiological parameter; and adjusting output power of the audio outputting unit based on the audio adjustment parameter, and controlling the audio outputting unit to output audio information at the adjusted output power, so that the outputted audio information coincides with the outputted adjusted image information.

9 Claims, 4 Drawing Sheets

(51) Int. Cl.
*A61B 5/11* (2006.01)
*A61B 3/113* (2006.01)
*G06T 19/00* (2011.01)
*G06F 3/0482* (2013.01)

(56) References Cited

U.S. PATENT DOCUMENTS

| | | | | |
|---|---|---|---|---|
| 2002/0071661 | A1* | 6/2002 | Nakano | G11B 27/031 386/230 |
| 2013/0246967 | A1* | 9/2013 | Wheeler | G06F 3/012 715/784 |
| 2014/0176813 | A1* | 6/2014 | Conness | H04N 5/60 348/738 |
| 2014/0375541 | A1* | 12/2014 | Nister | G06F 3/013 345/156 |
| 2015/0055808 | A1* | 2/2015 | Vennstrom | G06F 3/167 381/307 |
| 2015/0338915 | A1* | 11/2015 | Publicover | H04N 5/23229 345/633 |
| 2016/0313973 | A1* | 10/2016 | Yajima | G06F 3/165 |
| 2017/0078825 | A1* | 3/2017 | Mangiat | H04S 7/40 |

* cited by examiner

METHOD AND DEVICE FOR ADJUSTING AUDIO AND VIDEO BASED ON A PHYSIOLOGICAL PARAMETER OF A USER

CROSS REFERENCE OF RELATED APPLICATION

This application claims the priority to Chinese Patent Application No. 201510618003.6, entitled "INFORMATION PROCESSING METHOD AND ELECTRONIC DEVICE", filed with the Chinese State Intellectual Property Office on Sep. 24, 2015, which is incorporated by reference in its entirety herein.

FIELD

The disclosure relates to the intelligent terminal technology in the communication field, and in particular to an information processing method and an electronic device.

BACKGROUND

A stereophonic sound is a sound having a sense of direction caused by difference in sounds heard by left and right ears. In a virtual reality player (VR Player), a real picture seen by a user may be changed due to an action of turning round his head or a viewpoint switching of the user. However, telepresence dislocation of the sound may be caused since sounds in each sound channel of audio outputting unit in the VR Player are outputted as they are.

SUMMARY

In view of the technical problems in the conventional art, an information processing method and an electronic device are provided according to the embodiments of the present disclosure.

For the above purposes, the technical solutions according to the present disclosure are achieved as follows.

An information processing method applicable to an electronic device is provided according to an embodiment of the present disclosure. The electronic device includes at least a fixing unit, and the electronic device is fixed onto a part of a user via the fixing unit. The method includes:

detecting a first physiological parameter of the user;

obtaining a change in the first physiological parameter of the user based on the first physiological parameter of the user;

controlling, based on the change in the first physiological parameter of the user, an image outputting unit to output adjusted image information;

determining an audio adjustment parameter for an audio outputting unit based on the change in the first physiological parameter; and adjusting output power of the audio outputting unit based on the audio adjustment parameter, and controlling the audio outputting unit to output audio information at the adjusted output power, where the outputted audio information coincides with the outputted adjusted image information.

An electronic device is provided according to an embodiment of the present disclosure. The electronic device includes:

a fixing unit, where the electronic device is fixed onto a part of a user via the fixing unit;

an acquisition unit configured to detect a first physiological parameter of the user; and a processing unit configured to obtain a change in the first physiological parameter of the user based on the first physiological parameter of the user; control, based on the change in the first physiological parameter of the user, an image outputting unit to output adjusted image information; determine an audio adjustment parameter for an audio outputting unit based on the change in the first physiological parameter; and adjust output power of the audio outputting unit based on the audio adjustment parameter, and control the audio outputting unit to output audio information at the adjusted output power, where the outputted audio information coincides with the outputted adjusted image information.

With the information processing method and the electronic device according to the present disclosure, the first physiological parameter of the user is acquired, the image information to be outputted by the image outputting unit is adjusted based on the change in the first physiological parameter, the audio adjustment parameter for the audio outputting unit is determined based on the change in the first physiological parameter, and the output power of the audio outputting unit is adjusted based on the audio adjustment parameter. In this way, audio outputted by the audio outputting unit coincides with an image outputted by the image outputting unit, thereby ensuring coincidence between visual and auditory direction-senses and improving user experience in using the electronic device.

DETAILED DESCRIPTION OF THE EMBODIMENTS

Hereinafter, the present disclosure is explained in further detail in conjunction with the drawings and specific embodiments.

First Embodiment

Figure 1:
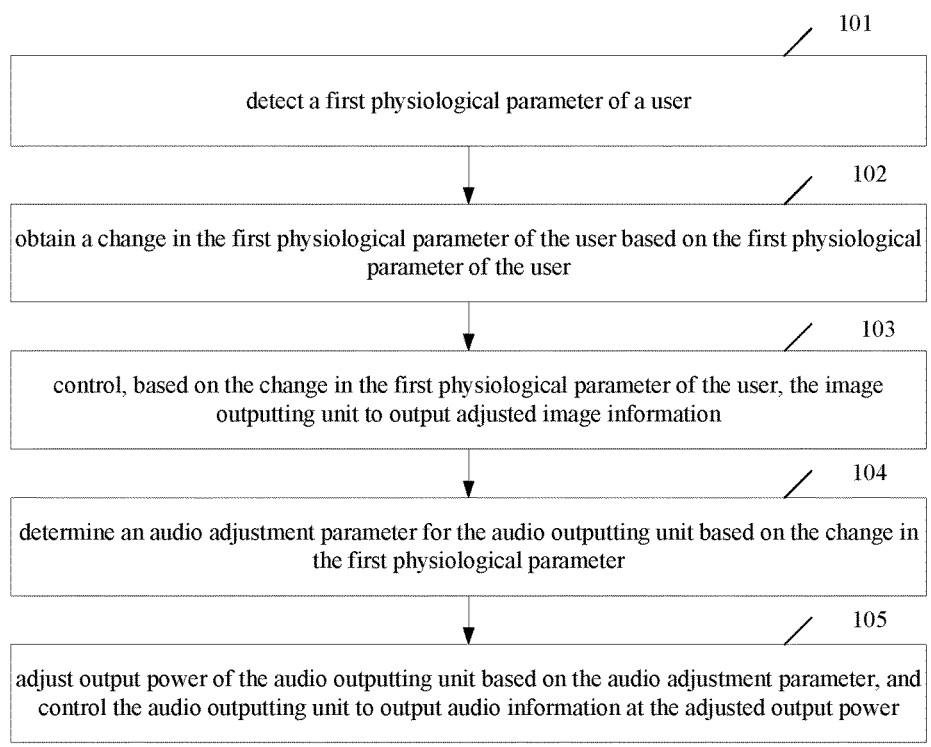
FIG. 1 is a schematic flowchart of an information processing method according to an embodiment of the present disclosure.

An information processing method applicable to an electronic device is provided according to an embodiment of the present disclosure. The electronic device includes at least a fixing unit, an image outputting unit and an audio outputting unit. The electronic device is fixed onto a part of a user via the fixing unit. As shown in FIG. 1, the method includes:

step 101: detecting a first physiological parameter of the user;

step 102: obtaining a change in the first physiological parameter of the user based on the first physiological parameter of the user;

step 103: controlling, based on the change in the first physiological parameter of the user, the image outputting unit to output adjusted image information;

step 104: determining an audio adjustment parameter for the audio outputting unit based on the change in the first physiological parameter; and step 105: adjusting output power of the audio outputting unit based on the audio adjustment parameter, and controlling the audio outputting unit to output audio information at the adjusted output power, where the outputted audio information coincides with the outputted adjusted image information.

Figure 2:
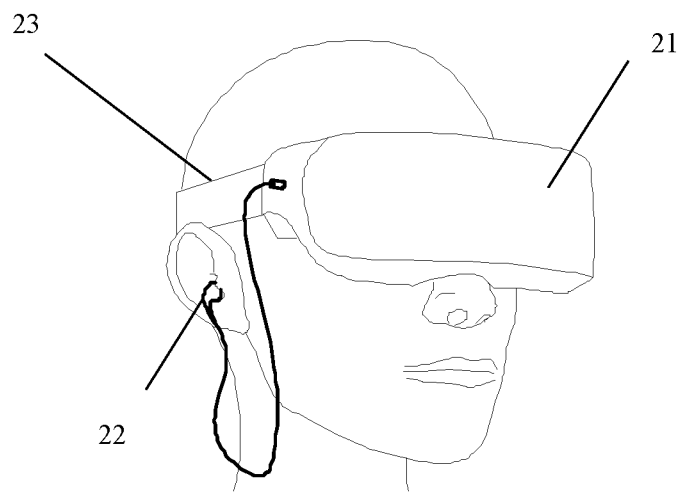
FIG. 2 is a schematic diagram of a first usage scenario according to an embodiment of the present disclosure.

Here, the electronic device may be a VR player. As shown in FIG. 2, an image outputting unit 21 may be disposed in an area close to eyes of the user, so that a corresponding image is seen by the user via the image outputting unit. The image according to the embodiment may include multiple frames of images. That is, an output from the image outputting unit may be a video. An audio outputting unit 22 may be a headphone. A fixing unit 23 may be a device capable of fixing the electronic device onto the eyes, as shown in the drawings, such as an elastic adjustable bandage.

The detecting the first physiological parameter of the user according to the embodiment may include acquiring periodically an eye parameter of the user via an acquisition unit; and the obtaining the change in the first physiological parameter of the user based on the first physiological parameter of the user may include:

determining an eye movement direction and an eye movement angle of the user based on the periodically acquired eye parameter of the user, and setting the eye movement direction and the eye movement angle as the change in the first physiological parameter of the user.

Figure 3:
FIG. 3 is a schematic positional diagram of an acquisition unit according to an embodiment of the present disclosure.

The acquisition unit may be a camera. The number of cameras in the acquisition unit may be one or two. For example, two cameras may be disposed on left and right eyes respectively to acquire the eye parameter of the user, in a case that the electronic device is worn on the eyes of the user. As shown in FIG. 3, it is provided that a side of the electronic device capable of being seen from a visual angle close to the eye of the user is a first side of the electronic device. Two cameras 311 and 312 are provided on the first side. Alternatively, only one camera may be disposed. Alternatively, only one of the cameras may be opened, for example the left camera 311 may be opened.

The embodiment may be explained by taking adopting only the camera 311 as an example. A parameter of a pupil or a black eyeball of the user is acquired periodically by the camera 311 as the eye parameter. An eye parameter acquired during a current cycle is compared with an eye parameter acquired during a last cycle, to obtain a movement direction and a movement angle of the pupil in the eye of the user as the change in the first physiological parameter.

The controlling the image outputting unit to output the adjusted image information includes:

determining an adjustment direction and an adjustment distance for the image information based on the eye movement direction and the eye movement angle of the user;

obtaining, based on the adjustment direction and the adjustment distance, adjusted image information which is to be outputted; and controlling the image outputting unit to output the adjusted image information.

The determining an adjustment direction and an adjustment distance for the image information based on the eye movement direction and the eye movement angle of the user may be implemented in two ways as follows.

In a first way, the adjustment direction for the image information is determined firstly based on the eye movement direction; and the adjustment distance for the image information is selected from a preset first correspondence list based on the eye movement angle.

In a second way, the adjustment direction for the image information is determined firstly based on the eye movement direction; and the adjustment distance for the image information is calculated based on the eye movement angle.

The calculated adjustment distance for the image information may be a displacement of the viewpoint of the user in the image display unit of the electronic device, which is calculated based on a first distance between the user and the electronic device and the eye movement angle.

Figure 4:
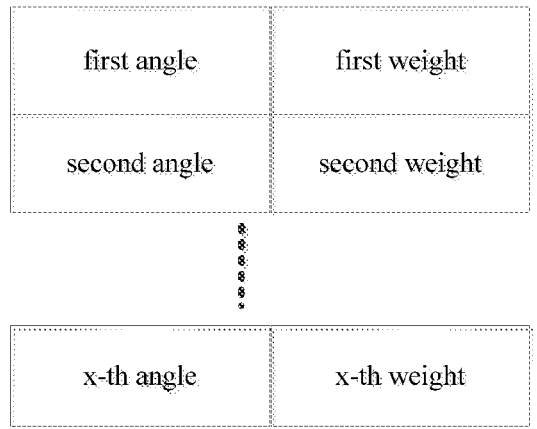
FIG. 4 is a schematic diagram of a preset list according to an embodiment of the present disclosure.

The audio adjustment parameter may be determined in the following way according to the embodiment:

presetting an audio adjustment parameter list, where the audio adjustment parameter list includes at least one weight corresponding to the change in the first physiological parameter. For example, the eye parameter is the first physiological parameter, and the change in the first physiological parameter is the eye movement direction and the eye movement angle. The audio adjustment parameter list may include a first angle and a first weight corresponding to the first angle; and a second angle and a second weight corresponding to the second angle, as shown in FIG. 4.

The determining the audio adjustment parameter for the audio outputting unit based on the change in the first physiological parameter includes: selecting a first weight from the preset audio adjustment parameter list based on the change in the first physiological parameter; and determining audio adjustment parameters for at least two audio outputting sub-units of the audio outputting unit based on the first weight.

The determining audio adjustment parameters for at least two audio outputting sub-units of the audio outputting unit based on the first weight may include: calculating at least two weights of at least two audio outputting sub-units of the audio outputting unit based on the first weight, and setting a matrix built based on the at least two weights as the audio adjustment parameter.

Taking the audio outputting unit including two audio outputting sub-units as an example, as shown in FIG. 2, the audio outputting unit includes two outputting sub-units: a left channel and a right channel. The first weight may be a weight for the left channel.

A second weight may be calculated based on the first weight. The second weight may be obtained by subtracting the first weight from a cardinal number.

The matrix constituted of the first weight and the second weight is set as the audio adjustment parameter.

A method for using the audio adjustment parameter may include: multiplying the audio adjustment parameter by a matrix constituted of output powers of two outputting sub-units, and setting the productions as the adjusted output powers for the two outputting sub-units.

As can be seen, with the above solution, the first physiological parameter of the user is acquired, the image information to be outputted by the image outputting unit of the electronic device is adjusted based on the change in the first physiological parameter, the audio adjustment parameter for the audio outputting unit is determined based on the change in the first physiological parameter, and the output power of the audio outputting unit is adjusted based on the audio adjustment parameter. In this way, audio outputted by the audio outputting unit coincides with an image outputted by the image outputting unit, thereby ensuring coincidence between visual and auditory direction-senses and improving user experience in using the electronic device.

Second Embodiment

An information processing method applicable to an electronic device is provided according to an embodiment of the present disclosure. The electronic device includes at least a fixing unit, an image outputting unit and an audio outputting unit. The electronic device is fixed onto a part of a user via the fixing unit. As shown in FIG. 1, the method includes:

step 101: detecting a first physiological parameter of the user;

step 102: obtaining a change in the first physiological parameter of the user based on the first physiological parameter of the user;

step 103: controlling, based on the change in the first physiological parameter of the user, the image outputting unit to output adjusted image information;

step 104: determining an audio adjustment parameter for the audio outputting unit based on the change in the first physiological parameter; and step 105: adjusting output power of the audio outputting unit based on the audio adjustment parameter, and controlling the audio outputting unit to output audio information at the adjusted output power, where the outputted audio information coincides with the outputted adjusted image information.

Here, the electronic device may be a VR player. As shown in FIG. 2, an image outputting unit 21 may be disposed in an area close to eyes of the user, so that the user sees a corresponding image via the image outputting unit. The image according to the embodiment may include multiple frames of images. That is, an output from the image outputting unit may be a video. An audio outputting unit 22 may be a headphone. A fixing unit 23 may be a device capable of fixing the electronic device onto the eyes, as shown in the drawings, such as an elastic adjustable bandage.

The detecting the first physiological parameter of the user according to the embodiment may include acquiring periodically an eye parameter of the user via an acquisition unit; and the obtaining the change in the first physiological parameter of the user based on the first physiological parameter of the user may include:

determining an eye movement direction and an eye movement angle of the user based on the periodically acquired eye parameter of the user, and setting the eye movement direction and the eye movement angle as the change in the first physiological parameter of the user.

The acquisition unit may be a camera. Further, the number of cameras in the acquisition unit may be one or two. For example, two cameras may be disposed on left and right eyes respectively to acquire the eye parameter of the user, in a case that the electronic device is worn on the eyes of the user. As shown in FIG. 3, it is provided that a side of the electronic device capable of being seen from a visual angle close to the eye of the user is a first side of the electronic device. Two cameras 311 and 312 are provided on the first side. Alternatively, only one camera may be disposed. Alternatively, only one of the cameras may be opened, and the left camera 311 may be reserved.

The embodiment may be explained by taking adopting only the camera 311 as an example. A parameter of a pupil or a black eyeball of the user is acquired periodically by the camera 311 as the eye parameter. An eye parameter acquired during a current cycle is compared with an eye parameter acquired during a last cycle, to obtain a movement direction and a movement angle of the pupil in the eye of the user as the change in the first physiological parameter.

The controlling the image outputting unit to output the adjusted image information includes:

determining an adjustment direction and an adjustment distance for the image information based on the eye movement direction and the eye movement angle of the user;

obtaining, based on the adjustment direction and the adjustment distance, adjusted image information which is to be outputted; and controlling the image outputting unit to output the adjusted image information.

The determining an adjustment direction and an adjustment distance for the image information based on the eye movement direction and the eye movement angle of the user may be implemented in two ways as follows.

In a first way, the adjustment direction for the image information is determined firstly based on the eye movement direction; and the adjustment distance for the image information is selected from a preset first correspondence list based on the eye movement angle.

In a second way, the adjustment direction for the image information is determined firstly based on the eye movement direction; and the adjustment distance for the image information is calculated based on the eye movement angle.

The calculated adjustment distance for the image information may be a displacement of the viewpoint of the user in the image display unit of the electronic device, which is calculated based on a first distance between the user and the electronic device and the eye movement angle.

The audio adjustment parameter may be determined as follows according to the embodiment.

The determining the audio adjustment parameter for the audio outputting unit based on the change in the first physiological parameter may include:

obtaining a first weight by doing remainder to the change in the first physiological parameter and a first number of audio outputting sub-units of the audio outputting unit; and determining the audio adjustment parameter for the audio outputting unit based on the first weight.

The obtaining the first weight by doing remainder to the change in the first physiological parameter and the first number of audio outputting sub-units of the audio outputting unit may use the following equation:

$$w1 = \left(\theta\% \frac{360}{n}\right) * \frac{n}{360};$$

where θ indicates the eye movement angle in the change in the first physiological parameter; "%" indicates a remainder calculation; and n indicates the first number, which is the number of the sub-units in a current audio outputting unit, which also is the number of sound channels of the audio outputting unit. The number of the channels in the VR Player is generally 2, that is, n=2.

The determining the audio adjustment parameter for the audio outputting unit based on the first weight may include:

obtaining at least one second weight corresponding to audio outputting sub-units other than an audio outputting sub-unit corresponding to the first weight in the current audio outputting unit based on the first weight; and setting a matrix constituted of the first weight and the at least one second weight as the audio adjustment parameter for the audio outputting unit.

In the embodiment, the audio outputting unit including two audio outputting sub-units is taken as an example. It is provided that the first weight indicates a weight of an audio outputting sub-unit corresponding to the left channel among two audio outputting sub-units. The second weight of an audio outputting sub-unit corresponding to the right channel may be calculated based on the first weight as follow: w2=1−w1; where w1 is the first weight, and w1 is calculated as above, which is not described here.

The audio adjustment parameter may be obtained based on the matrix constituted of the first weight and the second weight as follow:

$$\begin{bmatrix} w1 & w2 \\ 0 & w1 \end{bmatrix}.$$

The adjusting output power of the audio outputting unit based on the audio adjustment parameter according to the embodiment may include: setting output powers of the audio outputting sub-units in the current audio outputting unit as initial output powers; forming a matrix by the initial output powers; and obtaining adjusted output power of the audio outputting unit by multiplying the matrix constituted of the initial output powers by the audio adjustment parameter.

Taking two audio outputting sub-units as an example, the adjusted output power is calculated as follow:

$$\begin{bmatrix} v1' \\ v2' \end{bmatrix} = \begin{bmatrix} w1 & w2 \\ 0 & w1 \end{bmatrix} \times \begin{bmatrix} v1 \\ v2 \end{bmatrix};$$

where v1 and v2 indicate initial output powers of the audio outputting sub-units, and v1' and v2' are the adjusted output powers.

It can be understood that, although the embodiment is described by taking two outputting sub-units as an example, the above audio adjustment parameter may be adjusted as follow, in a case that the VR player outputs sound via five sound channels with the development of technology:

$$\begin{bmatrix} v1' \\ v2' \\ v3' \\ v4' \\ v5' \end{bmatrix} = \begin{bmatrix} w11 & w12 & w13 & w14 & w15 \\ w21 & w22 & w23 & w24 & w25 \\ w31 & w32 & w33 & w34 & w35 \\ w41 & w42 & w43 & w44 & w45 \\ w51 & w52 & w53 & w54 & w55 \end{bmatrix} \times \begin{bmatrix} v1 \\ v2 \\ v3 \\ v4 \\ v5 \end{bmatrix}.$$

Where w11 to w55 are calculated in a method similar to the above method for calculating the two weights. For example, w11 to w15 may be calculated firstly, and then weights w2 to w5 are calculated based on w11 to w15. Initial output powers of the five outputting sub-units are v1, v2, v3, v4 and v5 respectively; and v1', v2', v3', v4' and v5' are the adjusted output powers.

In the above embodiment in which the audio is adjusted based on the eye movement, relative position of the eye of the user to the image outputting unit and the audio outputting unit is unfixed.

As can be seen, with the above solution, the first physiological parameter of the user is acquired, the image information to be outputted by the image outputting unit of the electronic device is adjusted based on the change in the first physiological parameter, the audio adjustment parameter for the audio outputting unit is determined based on the change in the first physiological parameter, and the output power of the audio outputting unit is adjusted based on the audio adjustment parameter. In this way, audio outputted by the audio outputting unit coincides with an image outputted by the image outputting unit, thereby ensuring coincidence between visual and auditory direction-senses and improving user experience in using the electronic device.

Third Embodiment

An information processing method applicable to an electronic device is provided according to an embodiment of the present disclosure. The electronic device includes at least a fixing unit, an image outputting unit and an audio outputting unit. The electronic device is fixed onto a part of a user via the fixing unit. As shown in FIG. 1, the method includes:

step 101: detecting a first physiological parameter of the user;

step 102: obtaining a change in the first physiological parameter of the user based on the first physiological parameter of the user;

step 103: controlling, based on the change in the first physiological parameter of the user, the image outputting unit to output adjusted image information;

step 104: determining an audio adjustment parameter for the audio outputting unit based on the change in the first physiological parameter; and step 105: adjusting output power of the audio outputting unit based on the audio adjustment parameter, and controlling the audio outputting unit to output audio information at the adjusted output power, where the outputted audio information coincides with the outputted adjusted image information.

Here, the electronic device may be a VR player. As shown in FIG. 2, an image outputting unit 21 may be disposed in an area close to eyes of the user, so that a corresponding image is seen by the user via the image outputting unit. The image according to the embodiment may include multiple frames of images. That is, an output from the image outputting unit may be a video. An audio outputting unit 22 may be a headphone. A fixing unit 23 may be a device capable of fixing the electronic device onto the eyes, as shown in the drawings, such as an elastic adjustable bandage.

The electronic device is fixed onto a head of the user via the fixing unit, and the detecting the first physiological parameter of the user may include acquiring periodically a head movement parameter of the user via an acquisition unit; and the obtaining the change in the first physiological parameter of the user based on the first physiological parameter of the user may include: determining a head movement direction and a head movement angle of the user based on the periodically acquired head movement parameter of the user; and setting the head movement direction and the head movement angle as the change in the first physiological parameter of the user.

Figure 5:
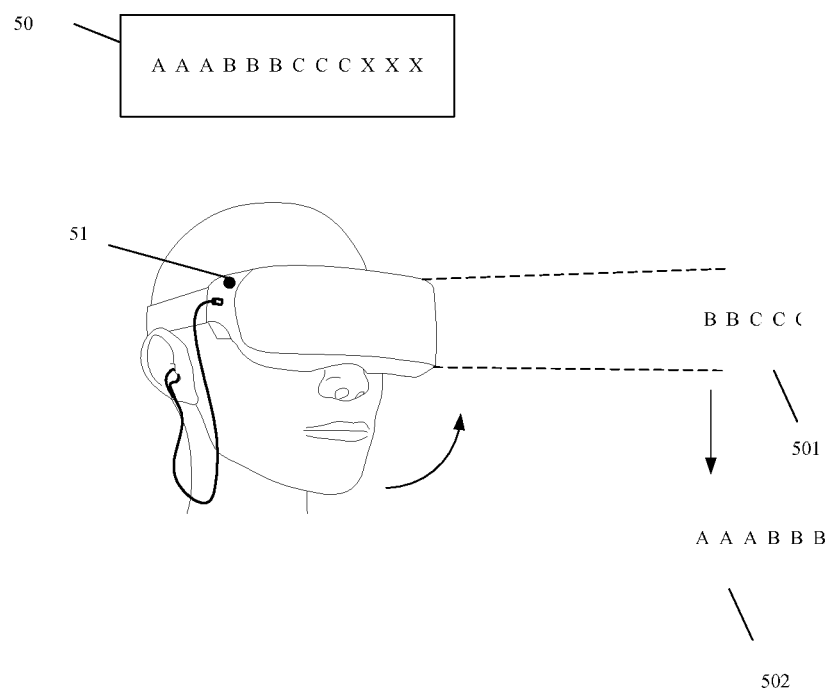
FIG. 5 is a schematic diagram of a second usage scenario according to an embodiment of the present disclosure.

The acquisition unit may be a sensor, such as an acceleration sensor. As shown in FIG. 5, the sensor may be disposed at a position 51.

The controlling the image outputting unit to output the adjusted image information includes:

determining an adjustment direction and an adjustment distance for the image information based on the head movement direction and the head movement angle of the user;

obtaining, based on the adjustment direction and the adjustment distance, adjusted image information which is to be outputted; and controlling the image outputting unit to output the adjusted image information.

The determining an adjustment direction and an adjustment distance for the image information based on the head movement direction and the head movement angle of the user may be implemented in two ways as follows.

In a first way, the adjustment direction for the image information is determined firstly based on the head movement direction; and the adjustment distance for the image information is selected from a preset first correspondence list based on the head movement angle.

In a second way, the adjustment direction for the image information is determined firstly based on the head movement direction; and the adjustment distance for the image information is calculated based on the head movement angle.

The calculated adjustment distance for the image information may be a displacement of the viewpoint of the user in the image display unit of the electronic device, which is calculated based on a first distance between the user and the electronic device and the head movement angle.

For example, as shown in FIG. 5, an initial image to be outputted is an image 50. An image which is can be seen by the user via the image outputting unit is shown as an image 501. A head rotating angle may be detected via the acceleration sensor as a first angle, in a case that the user turns the head in a direction indicated by the arrow.

A displacement of the viewpoint of the user in the image display unit of the electronic device is calculated as a displacement of the image 50 in the image display unit of the electronic device, and an outputted image is obtained as an image 502.

The audio adjustment parameter may be determined in two ways according to the embodiment.

In a first way, the determining the audio adjustment parameter for the audio outputting unit based on the change in the first physiological parameter includes: selecting a first weight from the preset audio adjustment parameter list based on the change in the first physiological parameter; and determining audio adjustment parameters for at least two audio outputting sub-units of the audio outputting unit based on the first weight.

The determining audio adjustment parameters for at least two audio outputting sub-units of the audio outputting unit based on the first weight may include: calculating at least two weights of at least two audio outputting sub-units of the audio outputting unit based on the first weight, and setting a matrix built based on the at least two weights as the audio adjustment parameter.

In a second way, the determining the audio adjustment parameter for the audio outputting unit based on the change in the first physiological parameter may include:

obtaining a first weight by doing remainder to the change in the first physiological parameter and a first number of audio outputting sub-units of the audio outputting unit; and determining the audio adjustment parameter for the audio outputting unit based on the first weight.

Specifically, the obtaining the first weight by doing remainder to the change in the first physiological parameter and the first number of audio outputting sub-units of the audio outputting unit may use the following equation:

$$w1 = \left(\theta\%\frac{360}{n}\right) * \frac{n}{360};$$

where $\theta$ indicates the eye movement angle in the change in the first physiological parameter; "%" indicates a remainder calculation; and n indicates the first number, which is the number of the sub-units in a current audio outputting unit, which also is the number of sound channels of the audio outputting unit. The number of the channels in the VR Player is generally 2, that is, n=2.

The determining the audio adjustment parameter for the audio outputting unit based on the first weight may include:

obtaining at least one second weight corresponding to audio outputting sub-units other than an audio outputting sub-unit corresponding to the first weight in the current audio outputting unit based on the first weight; and setting a matrix constituted of the first weight and the at least one second weight as the audio adjustment parameter for the audio outputting unit.

In the embodiment, the audio outputting unit including two audio outputting sub-units is taken as an example. It is provided that the first weight indicates a weight of an audio outputting sub-unit corresponding to the left channel among two audio outputting sub-units. The second weight of an audio outputting sub-unit corresponding to the right channel may be calculated based on the first weight as follow: w2=1−w1; where w1 is the first weight, and w1 is calculated as above, which is not described here.

The audio adjustment parameter may be obtained based on the matrix constituted of the first weight and the second weight as follow:

$$\begin{bmatrix} w1 & w2 \\ 0 & w1 \end{bmatrix}.$$

The adjusting output power of the audio outputting unit based on the audio adjustment parameter according to the embodiment may include: setting output powers of the audio outputting sub-units in the current audio outputting unit as initial output powers; forming a matrix by the initial output powers; and obtaining adjusted output power of the audio outputting unit by multiplying the matrix constituted of the initial output powers by the audio adjustment parameter.

Taking two audio outputting sub-units as an example, the adjusted output power is calculated as follow:

$$\begin{bmatrix} v1' \\ v2' \end{bmatrix} = \begin{bmatrix} w1 & w2 \\ 0 & w1 \end{bmatrix} \times \begin{bmatrix} v1 \\ v2 \end{bmatrix};$$

where v1 and v2 indicate initial output powers of the audio outputting sub-units, and v1' and v2' are the adjusted output powers.

It can be understood that, a scenario according to the embodiment in which movement of the head of the user initiates the image outputting unit to adjust the image which is to be outputted and initiates the audio outputting unit to adjust the audio output power, differs from a scenario in which the audio and the image are adjusted based on the eye movement in that, a relative position of the head of the user to the image outputting unit is fixed, and a relative position of the head of the user to the audio outputting unit is also fixed.

As can be seen, with the above solution, the first physiological parameter of the user is acquired, the image information to be outputted by the image outputting unit of the electronic device is adjusted based on the change in the first physiological parameter, the audio adjustment parameter for the audio outputting unit is determined based on the change in the first physiological parameter, and the output power of the audio outputting unit is adjusted based on the audio adjustment parameter. In this way, audio outputted by the audio outputting unit coincides with an image outputted by the image outputting unit, thereby ensuring coincidence between visual and auditory direction-senses and improving user experience in using the electronic device.

Fourth Embodiment

Figure 6:
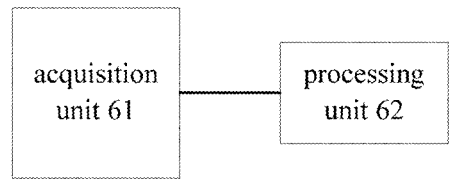
FIG. 6 is a schematic structural diagram of an electronic device according to an embodiment of the present disclosure.

An electronic device is provided according to an embodiment of the present disclosure. The electronic device includes at least a fixing unit, an image outputting unit and an audio outputting unit. The electronic device is fixed onto a part of a user via the fixing unit. As shown in FIG. 6, the electronic device further includes:

an acquisition unit 61 configured to detect a first physiological parameter of the user; and a processing unit 62 configured to obtain a change in the first physiological parameter of the user based on the first physiological parameter of the user; control, based on the change in the first physiological parameter of the user, the image outputting unit to output adjusted image information; determine an audio adjustment parameter for the audio outputting unit based on the change in the first physiological parameter; and adjust output power of the audio outputting unit based on the audio adjustment parameter, and control the audio outputting unit to output audio information at the adjusted output power, where the outputted audio information coincides with the outputted adjusted image information.

Here, the electronic device may be a VR player. As shown in FIG. 2, an image outputting unit 21 may be disposed in an area close to eyes of the user, so that a corresponding image is seen by the user via the image outputting unit. The image according to the embodiment may include multiple frames of images. That is, an output from the image outputting unit may be a video. An audio outputting unit 22 may be a headphone. A fixing unit 23 may be a device capable of fixing the electronic device onto the eyes, as shown in the drawings, such as an elastic adjustable bandage.

For detecting the first physiological parameter of the user according to the embodiment, the acquisition unit is configured to acquire periodically an eye parameter of the user; and the processing unit is configured to determine an eye movement direction and an eye movement angle of the user based on the periodically acquired eye parameter of the user; and set the eye movement direction and the eye movement angle as the change in the first physiological parameter of the user.

The acquisition unit may be a camera. The number of cameras in the acquisition unit may be one or two. For example, two cameras may be disposed on left and right eyes respectively to acquire the eye parameter of the user, in a case that the electronic device is worn on the eyes of the user. As shown in FIG. 3, it is provided that a side of the electronic device capable of being seen from a visual angle close to the eye of the user is a first side of the electronic device. Two cameras 311 and 312 are provided on the first side. Alternatively, only one camera may be disposed. Alternatively, only one of the cameras may be opened, and the left camera 311 may be reserved.

The embodiment may be explained by taking adopting only the camera 311 as an example. A parameter of a pupil or a black eyeball of the user is acquired periodically by the camera 311 as the eye parameter. An eye parameter acquired during a current cycle is compared with an eye parameter acquired during a last cycle, to obtain a movement direction and a movement angle of the pupil in the eye of the user as the change in the first physiological parameter.

The processing unit is configured to determine an adjustment direction and an adjustment distance for the image information based on the eye movement direction and the eye movement angle of the user; obtain, based on the adjustment direction and the adjustment distance, adjusted image information which is to be outputted; and control the image outputting unit to output the adjusted image information.

The determining an adjustment direction and an adjustment distance for the image information based on the eye movement direction and the eye movement angle of the user may be implemented in two ways as follows.

In a first way, the adjustment direction for the image information is determined firstly based on the eye movement direction; and the adjustment distance for the image information is selected from a preset first correspondence list based on the eye movement angle.

In a second way, the adjustment direction for the image information is determined firstly based on the eye movement direction; and the adjustment distance for the image information is calculated based on the eye movement angle.

The calculated adjustment distance for the image information may be a displacement of the viewpoint of the user in the image display unit of the electronic device, which is calculated based on a first distance between the user and the electronic device and the eye movement angle.

The audio adjustment parameter may be determined in the following way according to the embodiment:

presetting an audio adjustment parameter list, where the audio adjustment parameter list includes at least one weight corresponding to the change in the first physiological parameter. For example, the eye parameter is the first physiological parameter, and the change in the first physiological parameter is the eye movement direction and the eye movement angle. The audio adjustment parameter list may include a first angle and a first weight corresponding to the first angle; and a second angle and a second weight corresponding to the second angle, as shown in FIG. 4.

The processing unit is configured to select a first weight from the preset audio adjustment parameter list based on the change in the first physiological parameter; and determine audio adjustment parameters for at least two audio outputting sub-units of the audio outputting unit based on the first weight.

The processing unit is configured to calculate at least two weights of at least two audio outputting sub-units of the audio outputting unit based on the first weight, and set a matrix built based on the at least two weights as the audio adjustment parameter.

Taking the audio outputting unit including two audio outputting sub-units as an example, as shown in FIG. 2, the audio outputting unit includes two outputting sub-units: a left channel and a right channel. The first weight may be a weight for the left channel.

A second weight may be calculated based on the first weight. The second weight may be obtained by subtracting the first weight from a cardinal number.

The matrix constituted of the first weight and the second weight is set as the audio adjustment parameter.

A method for using the audio adjustment parameter may include: multiplying the audio adjustment parameter by a matrix constituted of output powers of two outputting sub-units, and setting the productions as the adjusted output powers for the two outputting sub-units.

The determining the audio adjustment parameter may be determined as follows according to the embodiment.

The processing unit is configured to:

obtain a first weight by doing remainder to the change in the first physiological parameter and a first number of audio outputting sub-units of the audio outputting unit; and determine the audio adjustment parameter for the audio outputting unit based on the first weight.

The obtaining the first weight by doing remainder to the change in the first physiological parameter and the first number of audio outputting sub-units of the audio outputting unit may use the following equation:

$$w1 = \left(\theta\% \frac{360}{n}\right) * \frac{n}{360};$$

where θ indicates the eye movement angle in the change in the first physiological parameter; "%" indicates a remainder calculation; and n indicates the first number, which is the number of the sub-units in a current audio outputting unit, which also is the number of sound channels of the audio outputting unit. The number of the channels in the VR Player is generally 2, that is, n=2.

The determining the audio adjustment parameter for the audio outputting unit based on the first weight may include:

obtaining at least one second weight corresponding to audio outputting sub-units other than an audio outputting sub-unit corresponding to the first weight in the current audio outputting unit based on the first weight; and setting a matrix constituted of the first weight and the at least one second weight as the audio adjustment parameter for the audio outputting unit.

In the embodiment, the audio outputting unit including two audio outputting sub-units is taken as an example. It is provided that the first weight indicates a weight of an audio outputting sub-unit corresponding to the left channel among two audio outputting sub-units. The second weight of an audio outputting sub-unit corresponding to the right channel may be calculated based on the first weight as follow: w2=1−w1; where w1 is the first weight, and w1 is calculated as above, which is not described here.

The audio adjustment parameter may be obtained based on the matrix constituted of the first weight and the second weight as follow:

$$\begin{bmatrix} w1 & w2 \\ 0 & w1 \end{bmatrix}.$$

The adjusting output power of the audio outputting unit based on the audio adjustment parameter according to the embodiment may include: setting output powers of the audio outputting sub-units in the current audio outputting unit as initial output powers; forming a matrix by the initial output powers; and obtaining adjusted output power of the audio outputting unit by multiplying the matrix constituted of the initial output powers by the audio adjustment parameter.

Taking two audio outputting sub-units as an example, the adjusted output power is calculated in the as follow:

$$\begin{bmatrix} v1' \\ v2' \end{bmatrix} = \begin{bmatrix} w1 & w2 \\ 0 & w1 \end{bmatrix} \times \begin{bmatrix} v1 \\ v2 \end{bmatrix};$$

where v1 and v2 indicate initial output powers of the audio outputting sub-units, and v1' and v2' are the adjusted output powers.

It can be understood that, although the embodiment is described by taking two outputting sub-units as an example, the above audio adjustment parameter may be adjusted as follow, in a case that the VR player outputs sound via five sound channels with the development of technology:

$$\begin{bmatrix} v1' \\ v2' \\ v3' \\ v4' \\ v5' \end{bmatrix} = \begin{bmatrix} w11 & w12 & w13 & w14 & w15 \\ w21 & w22 & w23 & w24 & w25 \\ w31 & w32 & w33 & w34 & w35 \\ w41 & w42 & w43 & w44 & w45 \\ w51 & w52 & w53 & w54 & w55 \end{bmatrix} \times \begin{bmatrix} v1 \\ v2 \\ v3 \\ v4 \\ v5 \end{bmatrix}.$$

Where w11 to w55 are calculated in a calculation method similar to a method for calculating the two weights. For example, w11 to w15 may be calculated firstly, and then weights w2 to w5 are calculated based on w11 to w15. Initial output power of the five outputting sub-units are v1, v2, v3, v4 and v5 respectively; and v1', v2', v3', v4' and v5' are the adjusted output powers.

As can be seen, with the above solution, the first physiological parameter of the user is acquired, the image information to be outputted by the image outputting unit is adjusted based on the change in the first physiological parameter, the audio adjustment parameter for the audio outputting unit is determined based on the change in the first physiological parameter, and the output power of the audio outputting unit is adjusted based on the audio adjustment parameter. In this way, audio outputted by the audio outputting unit coincides with an image outputted by the image outputting unit, thereby ensuring coincidence between visual and auditory direction-senses and improving user experience in using the electronic device.

Fifth Embodiment

An electronic device is provided according to an embodiment of the present disclosure. The electronic device includes at least a fixing unit, an image outputting unit and an audio outputting unit. The electronic device is fixed onto a part of a user via the fixing unit. As shown in FIG. 6, the electronic device further includes:

an acquisition unit 61 configured to detect a first physiological parameter of the user; and a processing unit 62 configured to obtain a change in the first physiological parameter of the user based on the first physiological parameter of the user; control, based on the change in the first physiological parameter of the user, the image outputting unit to output adjusted image information; determine an audio adjustment parameter for the audio outputting unit based on the change in the first physiological parameter; and adjust output power of the audio outputting unit based on the audio adjustment parameter, and control the audio outputting unit to output audio information at the adjusted output power, where the outputted audio information coincides with the outputted adjusted image information.

Here, the electronic device may be a VR player. As shown in FIG. 2, an image outputting unit 21 may be disposed in an area close to eyes of the user, so that a corresponding image is seen by the user via the image outputting unit. The image according to the embodiment may include multiple frames of images. That is, an output from the image outputting unit may be a video. An audio outputting unit 22 may be a headphone. A fixing unit 23 may be a device capable of fixing the electronic device onto the eyes, as shown in the drawings, such as an elastic adjustable bandage.

The electronic device is fixed onto a head of the user via the fixing unit, and the acquisition unit is configured to acquire periodically an eye parameter of the user.

The processing unit is configured to determine an eye movement direction and an eye movement angle of the user based on the periodically acquired eye parameter of the user; and set the eye movement direction and the eye movement angle as the change in the first physiological parameter of the user.

The acquisition unit may be a sensor, such as an acceleration sensor. As shown in FIG. 5, the sensor may be disposed at a position 51.

The processing unit is configured to determine an adjustment direction and an adjustment distance for the image information based on the head movement direction and the head movement angle of the user; obtain, based on the adjustment direction and the adjustment distance, adjusted image information which is to be outputted; and control the image outputting unit to output the adjusted image information.

The determining an adjustment direction and an adjustment distance for the image information based on the head movement direction and the head movement angle of the user may be implemented in two ways as follows.

In a first way, the adjustment direction for the image information is determined firstly based on the head movement direction; and the adjustment distance for the image information is selected from a preset first correspondence list based on the head movement angle.

In a second way, the adjustment direction for the image information is determined firstly based on the head movement direction; and the adjustment distance for the image information is calculated based on the head movement angle The calculated adjustment distance for the image information may be a displacement of the viewpoint of the user in the image display unit of the electronic device, which is calculated based on a first distance between the user and the electronic device and the head movement angle.

For example, as shown in FIG. 5, an initial image to be outputted is an image 50. An image which is can be seen by the user via the image outputting unit is shown as an image 501. A head rotating angle may be detected via the acceleration sensor as a first angle, in a case that the user turns the head in a direction indicated by the arrow.

A displacement of the viewpoint of the user in the image display unit of the electronic device is calculated as a displacement of the image 50 in the image display unit of the electronic device, and an outputted image is obtained as an image 502.

The audio adjustment parameter may be determined in two ways according to the embodiment.

In a first way, the processing unit is configured to: select a first weight from the preset audio adjustment parameter list based on the change in the first physiological parameter; and determine audio adjustment parameters for at least two audio outputting sub-units of the audio outputting unit based on the first weight.

The determining audio adjustment parameters for at least two audio outputting sub-units of the audio outputting unit based on the first weight may include: calculating at least two weights of at least two audio outputting sub-units of the audio outputting unit based on the first weight; and setting a matrix built based on the at least two weights as the audio adjustment parameter.

In a second way, the processing unit is configured to: obtain a first weight by doing remainder to the change in the first physiological parameter and a first number of audio outputting sub-units of the audio outputting unit; and determine the audio adjustment parameter for the audio outputting unit based on the first weight.

The obtaining the first weight by doing remainder to the change in the first physiological parameter and the first number of audio outputting sub-units of the audio outputting unit may use the following equation:

$$w1 = \left(\theta\% \frac{360}{n}\right) * \frac{n}{360};$$

where $\theta$ indicates the eye movement angle in the change in the first physiological parameter; "%" indicates a remainder calculation; and n indicates the first number, which is the number of the sub-units in a current audio outputting unit, which also is the number of sound channels of the audio outputting unit. The number of the channels in the VR Player is generally 2, that is, n=2.

The determining the audio adjustment parameter for the audio outputting unit based on the first weight may include:

obtaining at least one second weight corresponding to audio outputting sub-units other than an audio outputting sub-unit corresponding to the first weight in the current audio outputting units based on the first weight; and setting a matrix constituted of the first weight and the at least one second weight as the audio adjustment parameter for the audio outputting unit.

In the embodiment, the audio outputting unit including two audio outputting sub-units is taken as an example. It is provided that the first weight indicates a weight of an audio outputting sub-unit corresponding to the left channel among two audio outputting sub-units. The second weight of an audio outputting sub-unit corresponding to the right channel may be calculated based on the first weight as follow: w2=1−w1; where w1 is the first weight, and w1 is calculated as above, which is not described here.

The audio adjustment parameter may be obtained based on the matrix constituted of the first weight and the second weight as follow:

$$\begin{bmatrix} w1 & w2 \\ 0 & w1 \end{bmatrix}.$$

The adjusting output power of the audio outputting unit based on the audio adjustment parameter according to the embodiment may include: setting output powers of the audio outputting sub-units in the current audio outputting unit as initial output powers; forming a matrix by the initial output powers; and obtaining adjusted output power of the audio outputting unit by multiplying the matrix constituted of the initial output powers by the audio adjustment parameter.

Taking two audio outputting sub-units as an example, the adjusted output power is calculated as follow:

$$\begin{bmatrix} v1' \\ v2' \end{bmatrix} = \begin{bmatrix} w1 & w2 \\ 0 & w1 \end{bmatrix} \times \begin{bmatrix} v1 \\ v2 \end{bmatrix};$$

where v1 and v2 indicate initial output powers of the audio outputting sub-units, and v1' and v2' are the adjusted output powers.

It can be understood that, a scenario according to the embodiment in which movement of the head of the user initiates the image outputting unit to adjust the image which is to be outputted and initiates the audio outputting unit to adjust the audio output power, differs from a scenario in which the audio and the image are adjusted based on the eye movement in that, a relative position of the head of the user to the image outputting unit is fixed, and a relative position of the head of the user to the audio outputting unit is also fixed.

As can be seen, with the above solution, the first physiological parameter of the user is acquired, the image information to be outputted by the image outputting unit of the electronic device is adjusted based on the change in the first physiological parameter, the audio adjustment parameter for the audio outputting unit is determined based on the change in the first physiological parameter, and the output power of the audio outputting unit is adjusted based on the audio adjustment parameter. In this way, audio outputted by the audio outputting unit coincides with an image outputted by the image outputting unit, thereby ensuring coincidence between visual and auditory direction-senses and improving user experience in using the electronic device.

In several embodiments according to the present application, it should be understood that the disclosed device and method can be implemented in other ways. The device embodiments described above are merely schematic. For example, the division of the unit is merely a logic functional division, and there may be other divisions in practice. For example, multiple units or components can be combined, or can be integrated into another system, or some features can be ignored, or not be executed. In addition, the coupling, direct coupling or communication connection between components which are shown or discussed may be indirect coupling or communication connection via some interfaces, devices or units, which may be electrical, mechanical, or in other form.

The units illustrated as separate components may be or may not be separated physically, and the component displayed as a unit may be or may not be a physical unit. That is, the components may be located at the same place, or may be distributed on multiple network units, and some of or all of the units can be selected, as required, to realize the object of the solution of the embodiment.

The functional units in the embodiments of the present disclosure may be integrated in one processing module, or each of the units may be taken separately as a unit, or two or more units may be integrated into one unit. The above integrated unit can be implemented either in hardware, or in a combination of software and hardware functional units.

It is to be understood by those skilled in the art that all of or some of steps of the above method embodiments may be performed by instructing corresponding hardware through a program. The proceeding program may be stored in a computer readable storage medium. When being executed, the program performs the steps of the above method embodiments. The proceeding storage medium includes various mediums capable of storing program codes, such as a ROM, an RAM, a magnetic disc or an optic disc.

Specific embodiments of the present disclosure are disclosed as described above, but the scope of protection of the present disclosure is not limited thereto. Changes and alteration which may be thought in the technical scope disclosed by the present disclosure by one skilled in the art should fall within the scope of protection of the present disclosure. Therefore, the scope of protection of the present disclosure should be defined by the appended claims.

The invention claimed is:

1. An information processing method applicable to an electronic device, wherein the electronic device comprises at least a fixing unit, the electronic device is fixed onto a part of a user via the fixing unit, the method comprising:
periodically acquiring an eye parameter of the user via an acquisition unit as a first physiological parameter of the user;
determining an eye movement direction and an eye movement angle of the user based on the periodically acquired eye parameter of the user;
setting the eye movement direction and the eye movement angle as a change in the first physiological parameter of the user;
controlling, based on the change in the first physiological parameter of the user, an image outputting unit to output adjusted image information;
determining an audio adjustment parameter for an audio outputting unit based on the change in the first physiological parameter;
adjusting output power of the audio outputting unit based on the audio adjustment parameter;
controlling the audio outputting unit to output audio information at the adjusted output power, wherein the outputted audio information coincides with the outputted adjusted image information;
wherein the determining the audio adjustment parameter for the audio outputting unit based on the change in the first physiological parameter comprises:
obtaining a first weight based on the change in the first physiological parameter and a first number of audio outputting sub-units of the audio outputting unit; and
determining the audio adjustment parameter for the audio outputting unit based on the first weight,
wherein the first weight is obtained by using the following equation:

$$w1 = \left(\theta \% \frac{360}{n}\right) * \frac{n}{360},$$

wherein $\theta$ is the eye movement angle, % is defined as an operator symbol for a remainder calculation to calculate a remainder for a division of $\theta$ by $$\frac{360}{n},$$

and n is the first number.

2. An electronic device, comprising:
a fixing unit, wherein the electronic device is fixed onto a part of a user via the fixing unit;
an acquisition unit configured to periodically acquire an eye parameter of the user as a first physiological parameter of the user; and
a processing unit configured to determine an eye movement direction and an eye movement angle of the user based on the periodically acquired eye parameter of the user; set the eye movement direction and the eye movement angle as a change in the first physiological parameter of the user; control, based on the change in the first physiological parameter of the user, an image outputting unit to output adjusted image information; determine an audio adjustment parameter for an audio outputting unit based on the change in the first physiological parameter; adjust output power of the audio outputting unit based on the audio adjustment parameter; and control the audio outputting unit to output audio information at the adjusted output power, wherein the outputted audio information coincides with the outputted adjusted image information,
wherein the processing unit is further configured to:
obtain a first weight based on the change in the first physiological parameter and a first number of audio outputting sub-units of the audio outputting unit; and
determine the audio adjustment parameter for the audio outputting unit based on the first weight;
wherein the first weight is obtained by using the following equation:

$$w1 = \left(\theta \% \frac{360}{n}\right) * \frac{n}{360},$$

wherein $\theta$ is the eye movement angle, % is defined as an operator symbol for a remainder calculation to calculate a remainder for a division of $\theta$ by $$\frac{360}{n},$$

and n is the first number.

3. The method according to claim 1, wherein the determining the audio adjustment parameter for the audio outputting unit based on the change in the first physiological parameter comprises:
obtaining at least one second weight corresponding to audio outputting sub-units other than an audio outputting sub-unit corresponding to the first weight in the audio outputting unit based on the first weight; and
setting a matrix constituted of the first weight and the at least one second weight as the audio adjustment parameter for the audio outputting unit.

4. The electronic device according to claim 2, wherein the processing unit is further configured to:
obtain at least one second weight corresponding to audio outputting sub-units other than an audio outputting sub-unit corresponding to the first weight in the audio outputting unit based on the first weight; and
set a matrix constituted of the first weight and the at least one second weight as the audio adjustment parameter for the audio outputting unit.

5. The method according to claim 1, wherein the controlling the image outputting unit to output the adjusted image information comprises:
determining an adjustment direction and an adjustment distance for the image information based on the eye movement direction and the eye movement angle of the user, wherein the adjustment distance comprises a displacement of a viewpoint of the user in an image display unit of the electronic device, wherein the adjustment distance is calculated based on a first distance between the user and the electronic device and the eye movement angle of the user;
obtaining, based on the adjustment direction and the adjustment distance, adjusted image information which is to be outputted; and
controlling the image outputting unit to output the adjusted image information.

6. The electronic device according to claim 2, wherein the processing unit is configured to determine an adjustment direction and an adjustment distance for the image information based on the eye movement direction and the eye movement angle of the user; obtain, based on the adjustment direction and the adjustment distance, adjusted image information which is to be outputted; and control the image outputting unit to output the adjusted image information, wherein the adjustment distance comprises a displacement of a viewpoint of the user in an image display unit of the electronic device, wherein the adjustment distance is calculated based on a first distance between the user and the electronic device and the eye movement angle of the user.

7. An information processing method applicable to an electronic device, wherein the electronic device comprises at least a fixing unit, the electronic device is fixed onto a part of a user via the fixing unit, the method comprising:
periodically acquiring a head movement parameter of the user via an acquisition unit as a first physiological parameter of the user;
determining an head movement direction and an head movement angle of the user based on the periodically acquired head movement parameter of the user;
setting the head movement direction and the head movement angle as a change in the first physiological parameter of the user;
controlling, based on the change in the first physiological parameter of the user, an image outputting unit to output adjusted image information;
determining an audio adjustment parameter for an audio outputting unit based on the change in the first physiological parameter;
adjusting output power of the audio outputting unit based on the audio adjustment parameter; and
controlling the audio outputting unit to output audio information at the adjusted output power, wherein the outputted audio information coincides with the outputted adjusted image information;
wherein the determining the audio adjustment parameter for the audio outputting unit based on the change in the first physiological parameter comprises:
obtaining a first weight based on the change in the first physiological parameter and a first number of audio outputting sub-units of the audio outputting unit; and
determining the audio adjustment parameter for the audio outputting unit based on the first weight;
wherein the first weight is obtained by using the following equation:

$$w1 = \left(\theta\%\frac{360}{n}\right) * \frac{n}{360};$$

wherein θ is the head movement angle, % is defined as an operator symbol for a remainder calculation to calculate a remainder for a division of θ by $$\frac{360}{n},$$

and n is the first number.

8. The method according to claim 7, wherein the determining the audio adjustment parameter for the audio outputting unit based on the change in the first physiological parameter comprises:
  obtaining at least one second weight corresponding to audio outputting sub-units other than an audio outputting sub-unit corresponding to the first weight in the audio outputting unit based on the first weight; and
  setting a matrix constituted of the first weight and the at least one second weight as the audio adjustment parameter for the audio outputting unit.

9. The method according to claim 7, wherein the controlling the image outputting unit to output the adjusted image information comprises:
  determining an adjustment direction and an adjustment distance for the image information based on the head movement direction and the head movement angle of the user, wherein the adjustment distance comprises a displacement of a viewpoint of the user in an image display unit of the electronic device, wherein the adjustment distance is calculated based on a first distance between the user and the electronic device and the head movement angle of the user;
  obtaining, based on the adjustment direction and the adjustment distance, adjusted image information which is to be outputted; and
  controlling the image outputting unit to output the adjusted image information.

\* \* \* \* \*